United States Patent [19]

Acs et al.

[11] Patent Number: 4,642,205
[45] Date of Patent: Feb. 10, 1987

[54] DIASTEREOMER SALTS OF PHENYLALANINE AND N-ACYL DERIVATIVES THEREOF AND PROCESS FOR THE SEPARATION OF OPTICALLY ACTIVE PHENYLALANINE AND N-ACYL DERIVATIVES THEREOF

[75] Inventors: Maria Acs; Ferenc Faigl; Elemer Fogassy, all of Budapest, Hungary

[73] Assignee: Alkaloida Vegyēszeti Gyär, Postafiok, Hungary

[21] Appl. No.: 776,145

[22] PCT Filed: Mar. 1, 1985

[86] PCT No.: PCT/HU85/00012
§ 371 Date: Nov. 18, 1985
§ 102(e) Date: Nov. 18, 1985

[87] PCT Pub. No.: WO85/03932
PCT Pub. Date: Sep. 12, 1985

[30] Foreign Application Priority Data

Mar. 1, 1984 [HU] Hungary ................................ 824/84
Mar. 1, 1984 [HU] Hungary ................................ 825/84
Mar. 1, 1984 [HU] Hungary ................................ 826/84
Mar. 1, 1984 [HU] Hungary ................................ 827/84

[51] Int. Cl.[4] ................... C07C 83/00; C07C 83/08; C07B 57/00
[52] U.S. Cl. ........................ 260/501.17; 260/501.18; 562/401; 562/402
[58] Field of Search ............. 260/501.17, 501.18; 562/401, 402

[56] References Cited

U.S. PATENT DOCUMENTS 3,832,388 8/1974 Lorenz ............................ 562/401 X
4,151,198 4/1979 Halmos ........................... 562/401 X Primary Examiner—Natalie Trousof
Assistant Examiner—Vera C. Clarke
Attorney, Agent, or Firm—Karl F. Ross; Herbert Dubno

[57] ABSTRACT

The present invention relates to the separation of optically active phenylalanine and N-acyl derivatives thereof and novel diastereomer salts of the said compounds.

According to the invention a racemic compound of the formula

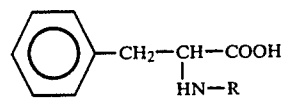

I is reacted with an optically active resolving agent of the formula

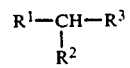

II in a polar solvent and/or a mixture of solvents comprising at least one apolar solvent and optionally an achiral acid or base, thereafter (a) when using the D-isomer of the resolving agent of the formula II, the crystalline diastereomer salt formed with the L-isomer of the compound of the formula I is separated, or (b) when using the L-isomer of the resolving agent of the formula II, the crystalline diastereomer salt formed with the D-isomer of the compound of the formula I is separated, and the enantiomers of the compound of the formula I from the diastereomer salt or the mother liquor are liberated by the aid of an achiral acid or base and the optically active product is separated in crystalline form.

8 Claims, No Drawings

DIASTEREOMER SALTS OF PHENYLALANINE AND N-ACYL DERIVATIVES THEREOF AND PROCESS FOR THE SEPARATION OF OPTICALLY ACTIVE PHENYLALANINE AND N-ACYL DERIVATIVES THEREOF

SPECIFICATION

TECHNICAL FIELD

The present invention relates to a process for the preparation of the enantiomers of phenylalanine

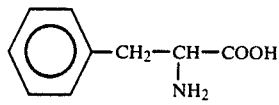

and of the N-acyl derivatives thereof by resolving the corresponding racemic compound. The resolution is carried out by forming new diastereomer salts of the different enantiomers.

Optically active phenylalanine is an amino acid produced on large scale. For example, the L-isomer is used for the synthesis of Aspartam ®️ (a dipeptide). In the course of the procedures for preparing racemic phenylalanine, the N-formyl or the N-acetyl derivative can be obtained directly in many cases, therefore the economic production of the phenylalanine enentiomers from the free amino acid or from the N-acyl derivatives thereof is of great importance from an industrial point of view.

No procedure is known in the prior art for resolving the racemate of the free acid. The phenylalanine enantiomers are prepared by using a phenylalanine derivative as starting material. It is reported that the phenylalanine alkyl esters can be resolved by an optically active acid (Belgian Patent Specification No. 795,874) and N-formyl-phenylalanine can be resolved by using optically active fenchilamine or by the aid of phenyl ethylamine in water (J. Am. Chem. Soc. 73, (1951)), by brucine in methanol (Liebigs Ann. Chem. 357, 1 (1907)) and by 2-aminobutanol in butanol as solvent (J. Am. Chem. Soc. 76, 2801 (1954)).

N-acetyl-phenylalanine can be resolved by using L-threo-2-amino-1,4-nitrophenyl propanediol in a polar solvent (J. Prakt. Chem. 9, 104 (1959)), by the aid of leucinamide in an alcoholic solvent (Agr. Biol. Chem. 26, 467 (1962)) and by using 2-(2,5-dimethylbenzylamino)-butanol in water as solvent (U.S. Pat. No. 4,151,198).

The above procedures have several disadvantages. They are quite expensive, toxic resolving agents have often to be used and the resolving agents are not always available in sufficient amount for industrial scale production. The yields are rather low and a product of appropriate purity can be obtained only after several recrystallization steps in many cases.

It was found that satisfactory separation can be achieved when compounds of the formula

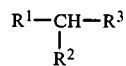

wherein a salt forming group containing a heteroatom, a polar substituent comprising an oxygen atom and an apolar substituent are directly attached to the chirality centre are used as resolving agents.

SUMMARY OF THE INVENTION

The present invention relates to novel diastereomer salts of phenylalanine and N-acyl derivatives thereof of the formula

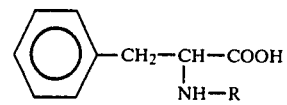

wherein
R is hydrogen or acyl, preferably formyl or acetyl, formed with optically active resolving agents of the formula

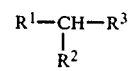

wherein
$R^1$ is carboxy, amino or benzylamino group,
$R^2$ is hydroxymethyl, benzoylamino, carbamoyl or benzoyloxy-carboxymethyl, the latter group being optionally substituted by an alkyl group on the benzene ring,
$R^3$ is alkyl, phenyl, phenylalkyl or benzoyloxy, the latter being optionally substituted by an alkyl group on the benzene ring.

Another object of the present invention is a process for the separation of enantiomers of the compound of the formula I and/or salts thereof.

According to the process of the invention the enantiomers of a racemic compound of the formula I and/or the salts thereof are reacted with an optically active resolving agent of the formula II in a polar solvent and/or a mixture of solvents comprising at least one apolar solvent and optionally an achiral acid or base, thereafter (a) when using the D-isomer of the resolving agent of the formula II, separating the crystalline diastereomer salt formed with the L-isomer of the compound of the formula I, or (b) when using the L-isomer of the resolving agent of the formula II, separating the crystalline diastereomer salt formed with the D-isomer of the compound of the formula I, and liberating the enantiomers of the compound of the formula I from the diastereomer salt or the mother liquor by the aid of an achiral acid or base and separating the optically active product in crystalline form.

DETAILED DESCRIPTION OF THE INVENTION

In the formula II the salt-forming group containing a heteroatom is represented by $R^1$, the polar substituent comprising an oxygen is represented by $R^2$, while the apolar substituent is represented by $R^3$.

Suitable alkyl groups which may be present in an optionally substituted benzoyloxy-carboxymethyl, benzoyloxy or phenylalkyl substituents include alkyl groups of 1 to 6 carbon atoms, preferably alkyl groups of 1 to 4 carbon atoms, more preferably methyl groups.

In the definition of $R^3$ alkyl may represent an alkyl group having 1 to 6, preferably 1 to 4 carbon atoms, more preferably methyl or ethyl group.

As compounds of the formula II most preferably the enantiomers of N-benzoyl phenylalanine, O,O-dibenzoyl tartaric acid, O,O-di-p-toluoyl tartaric acid, 2-benzoylbutanol or 2-phenylglycine amide can be used.

The diastereomer salts of the compounds of the formula I formed with the compounds of the formula II are novel compounds.

The preferred novel compounds according to the invention are as follows:

L-phenylalanine-D-N-benzoyl-phenylalanine salt,
D-phenylalanine-L-N-benzoyl-phenylalanine salt,
D-phenylalanine-O,O-dibenzoyl-L-tartaric acid salt,
D-phenylalanine-O,O-di-p-toluoyl-L-tartaric acid salt,
L-N-formyl-phenylalanine-D-2-benzylamino butanol salt,
L-N-acetyl-phenylalanyl-D-phenylglycine amide salt.

In the process of the invention racemic phenylalanine, racemic N-acyl-phenylalanine or the salts thereof can be used as starting materials. Suitable carboxylic acids from which an acyl group is derived include alkanoic acids having 1 to 8 carbon atoms, preferably having 1 to 4 carbon atoms, more preferably formic or acetic acid. Suitable salts include salts formed with organic or inorganic acids or bases, preferably with inorganic acids or bases, more preferably with hydrochloric acid, sodium or ammonium hydroxide.

According to the invention the diastereomer salt of the racemic compound of the formula I and the optically active compound of the formula II is prepared in the first step.

The formation of the diastereomer salt is suitably carried out in a solvent or a solvent mixture. If phenylalanine is used as starting material, water and/or an alcohol and/or an aromatic or halogenated hydrocarbon is used as solvent. Suitable alcohols include aliphatic alcohols, preferably aliphatic alcohols of 1 to 6 carbon atoms, more preferably methanol or ethanol. Suitable aromatic or halogenated hydrocarbons include e.g. benzene, toluene, chloroform or dichloroethane.

If an N-acyl-derivative of phenylalanine is used as starting material, water and/or a water-miscible organic solvent can be used as solvent. Suitable water-miscible organic solvents include preferably polar organic solvents, more preferably acetone.

The solvent used in the salt formation step optionally contains an achiral acid or base. Suitable achiral acids include organic or inorganic acids, preferably strong inorganic acids, more preferably hydrochloric, sulphuric or nitric acid. Suitable achiral bases include organic or inorganic bases, preferably sodium or ammonium hydroxide.

In the course of the salt formation one of the stereoisomers of phenylalanine or an N-acyl derivative therof forms a crystalline diastereomer salt, while the other isomer remains in the solution in the form of a salt formed with the resolving agent or with the achiral acid or base used as an additive. When the suitable ratio of the resolving agent to the achiral acid or base is chosen, almost quantitative separation can be achieved.

If desired, the diastereomer salts prepared according to the invention can be purified by recrystallization.

To the diastereomer salts prepared according to the invention or to the mother liquors thereof a polar solvent or mixture of polar solvents, preferably water and/or alcohol thereafter an achiral acid or base are added and the optically active phenylalanine, the salt or N-acyl derivative thereof precipitates in crystalline form. The achiral acid or base and the alcohol may be the same as defined in the salt formation step.

If desired the resolving agent can be firstly precipitated from the solution of the diastereomer salt or from the mother liquor obtained after the filtration of the diastereomer salt. Then a precipitating agent, an acid or a base, corresponding to the chemical character of the resolving agent is added to the solution and the optically active agent is precipitated from the mother liquor by adjusting the suitable pH.

The salt of the optically active compound can also be prepared by simple distillation of the mother liquor obtained after precipitating the resolving agent and thereafter by crystallization of the desired product.

The optical purity of the enantiomers of the compounds of the formula I obtained by decomposing the diastereomer salts and working up the filtrates of the salt forming reactions can be enhanced by fractionated, selective precipitation. Then the raw material is dissolved in the molar equivalent amount of a base or acid (chosen by considering the chemical character of the compound in question). The acids or bases listed hereinabove can be used in the process. An acid or base corresponding to the racemic compound content of the solution calculated from the optical activity of the raw material is added and the crystalline product having a composition similar to the racemic composition is filtered off. Adjusting the pH of the filtrate to the suitable value, the optically active phenylalanine or the derivative thereof can be precipitated.

When the isomers of the raw material or the salts thereof are purified by recrystallization, always the optically pure portion crystallizes from the solvent used.

The economy of our process is increased by regenerating the resolving agents and recirculating the racemic compound of the formula I obtained in the purification step.

The process according to the invention is illustrated by the following, non-limiting examples.

EXAMPLE 1

6.6 g of racemic phenylalanine are boiled in a mixture of 4 ml of 5M hydrochloric acid and 50 ml of water until the total amount of phenylalanine is dissolved. 5.4 g of D-N-benzoyl-phenylalanine in 20 ml of methanol are added to the hot solution under stirring and the solution is allowed to cool. The reaction mixture is stirred at room temperature for 2 hours, then the crystalline L-phenylalanine-D-N-benzoylphenylalanine salt is filtered off, washed with water and dried. The salt weights 8 g. M.p.: 175°–176° C. The salt is suspended in 30 ml of water, then 2.5 ml of concentrated hydrochloric acid are added and the solution is stirred for one hour. The precipitated crystalline D-N-benzoylphenylalanine is filtered off, washed with water and dried. Its weight is 4.9 g. M.p.: 140°–142° C.

The filtrate obtained after the decomposition of the salt is evaporated to the half of its original volume and the pH of the distillation residue thus obtained is adjusted to 6 by adding 5M sodium hydroxide solution. After cooling with ice for 1 hour the precipitated L-phenylalanine is filtered off, washed with water and dried. Weight: 2.65 g. $[\alpha]_D = -35°$ (c=1.3, water). To the mother liquor obtained upon filtrating the diastereomer salt 0.5 ml of concentrated hydrochloric acid are added and the solution is evaporated to 20 ml volume in vacuo. The warm mixture is clarified by charcoal and adjusted to pH 6 by adding 5M sodium hydroxide solution. The precipitated D-phenylalanine is filtered off, washed with water and dried. The weight of the product is 3.2 g. $[\alpha] = +32°$ (c=1, water).

EXAMPLE 2

6.6 g of racemic phenylalanine are boiled in a mixture of 3.6 ml 6M hydrochloric acid and 45 ml of water until the total amount of phenylalanine is dissolved. A mixture of 6 g L-N-benzoyl-phenylalanine and 20 ml of methanol are added under stirring. The solution is cooled and stirred for two hours at a temperature of 10° C. The crystalline D-phenylalanine-L-N-benzoyl-phenylalanine salt is filtered off, washed with water and dried. Its weight is 9 g.

The salt is suspended in 40 ml of water, then 3 ml of concentrated hydrochloric acid are added. The precipitated L-N-benzoyl-phenylalanine is filtered off, washed with water and dried. Its weight amounts to 5.4 g. M.p.: 140°–142° C. The filtrate obtained in the course of the salt decompositon step is evaporated to dryness, the residue is dissolved in 30 ml of methanol and the pH of the solution is adjusted to 6 by adding aqueous ammonia at 50° C. The precipitated D-phenylalanine is filtered off after one hour of cooling, washed with methanol and dried. The weight of the product is 3.2 g. $[\alpha]_D = +30°$ (c=1, water).

The mother liquor obtained in the salt decomposition step is evaporated to dryness in vacuo and the residue is worked up as described for the filtrate of the salt decomposition step. The L-phenylalanine precipitated is filtered off, washed with methanol and dried. The weight of the product is 3.0 g. $[\alpha]_D = -33.5°$. (c=1, water).

EXAMPLE 3

6.6 g of racemic phenylalanine are boiled in a mixture of 4 ml of 5M hydrochloric acid and 50 ml of water until the total amount of phenylalanine is dissolved, then 5 g of D-N-benzoyl-phenylalanine in 30 ml methanol are added under stirring. The L-phenylalanine-D-N-benzoyl-phenylalanine salt precipitated (7 g) is filtered off and dried. The salt is suspended in 20 ml of water and 2.5 ml of concentrated hydrochloric acid are added. The precipitated D-N-benzoyl-phenalalanine (4.3 g) is filtered off and dried.

The filtrate of the salt decomposition step is evaporated to dryness in vacuo, the residue is dissolved in 20 ml of ethanol and the pH of the solution is adjusted to 6 by adding aqueous ammonia. The crystalline L-phenylalanine is filtered off, washed with ethanol and dried. The weight of the product is 2.3 g. $[\alpha]_D = -35°$ (c=1, water).

To the filtrate obtained in the salt formation step 1 ml of concentrated hydrochloric acid is added and the solution is evaporated to dryness in vacuo. The residue is dissolved in 30 ml of ethanol and 2.5 ml of 5M aqueous ammonia are added. The composition of the precipitated phenylalanine is similar to the racemic composition. This racemic phenylalanine (1.7 g) is filtered off and dried. $[\alpha]_D = +4°$ (c=2, water). The pH of the filtrate is adjusted to 6 by adding aqueous ammonia, the precipitated D-phenylalanine is filtered off, washed with ethanol and dried. 2.3 g of the product are obtained. $[\alpha]_D = +34$ (c=1, water).

EXAMPLE 4

82.5 g of racemic phenylalanine and 100.8 g of racemic phenylalanine hydrochloride are dissolved in 1350 ml of water and a hot solution of 148 g of D-N-benzoyl-phenylalanine in 750 ml of methanol is added. The mixture is seeded by L-phenylalanine crystals and cooled to room temperature under stirring for 5 hours. The precipitated L-phenylalanine-D-N-benzoylphenylalanine salt is filtered off, washed with a mixture of water and methanol and dried. 191 g of the diastereomer salt are obtained. This diastereomer salt can be decomposed as follows:

(a) The wet salt is suspended in 750 ml of water, thereafter 100 ml of 10M hydrochloric acid are added. The precipitated D-N-benzoyl-phenylalanine is filtered off, washed with water and dried. Thus 124.6 g of resolving agent are recovered.

The mother liquor obtained in the salt decomposition step is extracted with dichloroethane. The remaining aqueous phase is evaporated to 180 g, then 70 ml of 10M hydrochloric acid are added to the solution and the mixture is cooled to 0° C. The precipitated L-phenylalanine hydrochloride is filtered off and dried. The weight of the product thus obtained is 76.2 g.

The filtrate obtained after precipitating the L-phenylalanine hydrochloride is evaporated to dryness in vacuo, washed with dichloroethane and dried. Thus a further amount of 1.8 g of L-phenylalanine hydrochloride are obtained.

The two fractions of L-phenylalanine hydrochloride are combined, dissolved in a mixture of 600 ml of hot methanol and 60 ml of water and the pH of the solution is adjusted to 6.5 with aqueous ammonia. The precipitated L-phenylalanine is filtered off, washed with methanol and dried. The weight of the product is 58 g. $[\alpha]_D = -34°$ (c=2, water).

(b) The dry diastereomer salt is suspended in 350 ml of methanol and a molar equivalent of aqueous ammonia is added. The precipitated L-phenylalanine is filtered at 20° C. and washed with methanol. 61 g of product are obtained. $[\alpha]_D = -33°$ (c=2, water).

The mother liquor obtained after precipitating the L-phenylalanine is evaporated to 300 g, then 800 ml water and 80 ml of 12M hydrochloric acid are added. The precipitated D-N-benzoyl-phenylalanine is filtered, washed with water and dried. 115 g of the resolving agent are recovered.

(c) The dry diastereomer salt is suspended in 400 ml of water, neutralized by adding a molar equivalent of aqueous ammonia. The then precipitated L-phenylalanine is dissolved by boiling the solution. The solution is clarified, filtered and cooled. The then precipitated L-phenylalanine is filtered at 10° C., washed with methanol and dried. 49 g of product are obtained. $[\alpha]_D = -34°$ (c=2, water).

The mother liquor is evaporated to 225 g, then 225 ml of methanol are added, the solution is cooled to 10° C. and the L-phenylalanine thus precipitated is filtered off. Thus a further amount of 10 g of the product are recovered. $[\alpha]_D = -32.5°$ (c=2, water).

The resolving agent can be recovered according to variant (b) of the salt decomposing step. The recovered resolving agent weights 118 g.

The mother liquor of the diastereomer salt formation step is evaporated to the half of its volume, then 20 ml of 12M hydrochloric acid are added. The precipitated resolving agent is filtered off, washed with water and dried. Thus 23 g of D-N-benzoyl-phenylalanine are obtained.

The filtrate is evaporated to 220 g, 100 ml of 10M hydrochloric acid are added to the hot solution and the mixture is cooled to 0° C. The precipitated D-phenylalanine-hydrochloride is filtered off and dried. 108.8 g of product are obtained.

Then the mother liquor is evaporated, the salt is washed with dichloroethane and dried. The weight of the D-phenylalanine hydrochloride thus obtained is 4 g.

EXAMPLE 5

3.3 g of D-phenylalanine of 85% optical purity are dissolved in a mixture of 15 ml of water and 2 ml of 5M hydrochloric acid, then 0.4 ml of 5M sodium hydroxide solution are added to the mixture. The composition of the precipitated phenylalanine is similar to the racemic composition. This precipitate is filtered off and dried. 0.6 g of racemic phenylalanine are obtained. $[\alpha]_D = +7°$ (c=2, water). The pH of the filtrate is adjusted to 6.5, then the precipitated D-phenylalanine is filtered at 0° C. and dried. The weight of the product is 2.3 g. $[\alpha]_D = +34°$ (c=1, water).

EXAMPLE 6

9.9 g of racemic phenylalanine are boiled in a mixture of 70 ml of water and 6 ml of 5M hydrochloric acid until the total amount of phenylalanine is dissolved and 11.3 g of O,O-dibenzoyl-L-tartaric acid monohydride dissolved in 30 ml methanol are added. The crystalline diastereomer salt is filtered at 25° C., washed with water and dried. 15.3 g of product are obtained. The salt is reacted with 50 ml of 12% hydrochloric acid, the precipitated resolving agent is filtered off, washed with water and dried. 10.6 g of product are obtained. M.p.: 89°–91° C.

The filtrate obtained in the course of the decomposition of the salt is evaporated to 20 ml and crystallized at 0° C. The precipitated D-phenylalanine hydrochloride is filtered off and dried. The weight of the product is 4.85 g $[\alpha]_D = +7.7°$ (c=3.5, 1N hydrochloric acid).

The remained mother liquor is evaporated to the half of its original volume and cooled with salted ice. The precipitated D-phenylalanine hydrochloride is filtered off and dried. 0.6 g of product are obtained. $[\alpha]_D = +3°$ (c=3, 1N hydrochloric acid).

The mother liquor obtained in the course of the salt formation step is evaporated to 20 ml, the hot solution is clarified and crystallized at 0° C. The precipitated L-phenylalanine hydrochloride is filtered off and dried. 4.5 g of product are obtained. $[\alpha]_D = -7.7°$ (c=4, 1N hydrochloric acid).

The residual mother liquor is evaporated to dryness, the residue is washed with dichloroethane, washed, filtered and dried. 1.6 g of product are obtained. $[\alpha]_D = -5°$ (c=4, 1N hydrochloric acid).

The amino acid enantiomers are obtained according to variant (a) of Example 4 from D-phenylalanine hydrochloride and L-phenylalanine hydrochloride.

EXAMPLE 7

6.6 g of racemic phenylalanine are dissolved in a hot mixture of 70 ml of water and 4 ml of 5M hydrochloric acid, thereafter 7.7 g of O,O-di-p-toluoyl-L-tartaric acid dissolved in 30 ml of ethanol are added. The procedure of Example 6 is followed. 10.3 g of the diastereomer salt and 3.1 g of D-phenylalanine hydrochloride liberated from the said salt are obtained. $[\alpha]_D = +7.3°$ (c=3, 1N hydrochloric acid). 3.44 g of L-phenylalanine are obtained from the mother liquor. $[\alpha]_D = -7.1°$ (c=4, 1N hydrochloric acid). 1.3 g of phenylalanine hydrochloride can be regenerated from the solutions obtained in the course of the working up of the salt and the mother liquor. $[\alpha]_D = 0°$ (c=3, 1N hydrochloric acid).

EXAMPLE 8

371.3 g of racemic phenylalanine and 554.1 g of racemic phenylalanine hydrochloride are boiled in 6800 ml of water until the total amount of the solid components are dissolved. Then a solution of 2500 ml of water and 846 g of O,O-dibenzoyl-L-tartaric acid monohydride is added. The solution is cooled to 25° C. and the precipitated diastereomer salt is filtered off and washed with a mixture of methanol and water. The wet salt is dissolved in a hot mixture of 2500 ml of water and 2500 ml of methanol, then the salt is recrystallized and filtered at 0° C. The wet salt is suspended in 2500 ml of water and 1150 ml of 10M hydrochloric acid are added, then the precipitated resolving agent is recovered by filtration at 0° C. and dried. 645 g of this agent are obtained. M.p.: 88°–90° C.

The filtrate obtained in the course of the decomposition of the salt is evaporated to 3000 ml, then 300 ml of dichloroethane are added to the residue and the phases are separated. The aqueous phase is evaporated to 1000 ml and the product is crystallized at 0° C. The D-phenylalanine hydrochloride is filtered off and dried. 290 g of this salt are obtained. The product is dissolved in a mixture of 1650 ml of methanol and 235 ml of water and the pH of the solution is adjusted to 6.5 by adding aqueous ammonia. The precipitated D-phenylalanine is filtered off, washed with methanol and dried. 220 g of product are obtained. $[\alpha]_D = +33.5°$ (c=2, water).

The mother liquor obtained in the course of the recrystallization of the diastereomer salt is evaporated to 800 ml and 375 ml of 10M hydrochloric acid are added. The precipitated O,O-dibenzoyl-L-tartaric acid is filtered and dried. 102 g of this acid are obtained. M.p.: 89°–90° C.

This filtrate and the filtrate obtained during the diastereomer salt formation step are combined and evaporated to 500 ml. 300 ml of dichloroethane are added to the residue, the aqueous phase is combined with the solution obtained in the course of precipitating D-phenylalanine hydrochloride and evaporated to 1600 ml. The optically not pure L-phenylalanine-hydrochloride is crystallized at 0° C. and filtered off. 690 g of this salt are obtained. The salt is dissolved in a mixture of 4000 ml of methanol and 500 ml of water and the pH of the solution thus obtained is adjusted to 6.5 by adding aqueous ammonia. The precipitated phenylalanine is filtered off and dried. 450 g of product are obtained. $[\alpha]_D = -15°$ (c=2, water).

EXAMPLE 9

690 g of L-phenylalanine hydrochloride prepared according to Example 8 are recrystallized from 1400 ml of methanol. The precipitated L-phenylalanine hydrochloride is filtered off at 5° C. and dried. 680 g of this salt are obtained. $[\alpha]_D = -7.7°$ (c=3.5, 1N hydrochloric acid). L-phenylalanine $[\alpha]_D = -33°$, (c=2, water)] is liberated according to Example 8 from this salt. The evaporation of the mother liquor obtained in the recrystallization step results in 700 g of phenylalanine hydrochloride. The composition of this salt is similar to the composition of the racemic mixture.

EXAMPLE 10

A mixture of 19.3 g of racemic N-formylphenylalanine and 17.9 g of D-2-benzylamino-butanol is boiled in 100 ml of acetone until the solid components are dissolved, thereafter the solution is allowed to cool. 17.1 g of L-N-formyl-phenylalanine-D-2-benzylamino-butanol are obtained after crystallization for 24 hours, filtration at 0° C. and drying.

To the diastereomer salt a mixture of 50 ml of water and 20 ml of 10M hydrochloric acid is added. L-N-formyl-phenylalanine is crystallized at 0° C., the precipitated product is filtered off, washed with water and dried. 8.5 g of the product are obtained. $[\alpha]_D = +62.3°$ (c=2, ethanol).

The mother liquor obtained in the diastereomer salt forming step is evaporated to dryness, then a mixture of 30 ml of water and 20 ml of 10M hydrochloric acid is added to the residue. 9.5 g of D-N-formyl-phenylalanine crystallizes from the solution at 0° C. $[\alpha]_D = -58.1°$ (c=2, ethanol).

The pH of the mixture of the hydrochloric solutions obtained in the course of the salt decomposition and the working up of the mother liquors is adjusted to 11 by adding 40% sodium hydroxide solution, then this solution is cooled to 0° C. The precipitated D-2-benzylamino-butanol is filtered off, washed with water and dried. 15 g of this resolving agent are obtained. $[\alpha]_D = -24.8°$ (c=2, ethanol).

EXAMPLE 11

15.7 g of racemic N-acetyl-phenylalanine are suspended in 35 ml of water and the pH of this solution is adjusted to 7 by adding aqueous ammonia. The mixture is heated until a clear solution is obtained, then 7.8 g of solid D-phenyl-glycine amide are added. The solution is cooled to 20° C. and kept at 0° C. for 12 hours. The formed L-N-acetyl-phenylalanyl-D-phenylglycineamide salt is removed by filtration. The weight of this salt is 11.7 g.

The decomposition of the diastereomer salt can be carried out as follows:

(a) 10 g of diastereomer salt are suspended in 20 ml of water, then 2 ml of 5M sodium hydroxide solution are added. The precipitated D-phenylglycine amide is filtered off, washed with water and dried. The weight of this amide is 3.6 g.

The mother liquor is acidified by 10 ml of 5M hydrochloric acid, the precipitated L-N-acetylphenylalanine is filtered off, washed with water and dried. 5.4 g of product are obtained. $[\alpha]_D = +43.2°$ (c=1, ethanol).

(b) 10 g of diastereomer salt are stirred with 30 ml of 5% hydrochloric acid solution. The undissolved L-N-acetyl-phenylalanine is filtered off, washed with water and dried. 5.2 g of product are obtained. $[\alpha]_D = +42°$ (c=1, ethanol).

The mother liquor obtained in the salt formation step is acidified by adding 5 ml of 10M hydrochloric acid. The precipitated D-N-acetyl-phenylalanine is filtered off, washed with water and dried. 8.1 g of product are obtained. $[\alpha]_D = -35.2°$ (c=1, ethanol).

8.1 g of D-N-acetyl-phenylalanine are suspended in 20 ml of water and the pH of the solution is adjusted to 7 by adding aqueous ammonia. 2.3 ml of 5M hydrochloric acid are added to the mixture thus obtained and the almost completely racemic precipitate is filtered off and dried. 2.3 g of the racemate are obtained. $[\alpha]_D = -3°$ (c=1, ethanol). Thereafter 3 ml of 10M hydrochloric acid are added to the filtrate and the precipitated D-N-acetyl-phenylalanine is filtered off, washed with water and dried. The weight of the product is 5.2 g $[\alpha]_D = -45°$ (c=1, ethanol).

What we claim is:

1. Process for the separation of the enantiomers of a racemic compound of the formula I

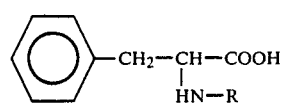

and/or the salts thereof, wherein

R is hydrogen or acyl, which comprises reacting a racemic compound of the formula I and/or the salt thereof with an optically active resolving agent of the formula

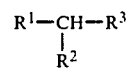

wherein $R^1$ is carboxy, amino or benzylamino group, $R^2$ is hydroxymethyl benzoylamino, carbamoyl or benzoyloxy-carboxymethyl, the latter group being optionally substituted by an alkyl group on the benzene ring, $R^3$ is alkyl, phenyl, phenylalkyl or benzoyloxy, the latter being optionally substituted by an alkyl group on the benzene ring, in a polar solvent and/or a mixture of solvents comprising at least one apolar solvent and optionally an achiral acid or base, thereafter (a) when using the D-isomer of the resolving agent of the formula II, separating the crystalline diastereomer salt formed with the L-isomer of the compound of the formula I, or (b) when using the L-isomer of the resolving agent of the formula II, separating the crystalline diastereomer salt formed with the D-isomer of the compound of the formula I, and liberating the enantiomers of the compound of the formula I from the diastereomer salt or the mother liquor by the aid of an achiral acid or base and separating the optically active product in crystalline form.

2. A process as claimed in claim 1 which comprises carrying out the formation of the diastereomer salt in the presence of a polar solvent, or a solvent mixture containing at least one aromatic hydrocarbon or halogenated hydrocarbon.

3. A process as claimed in claim 1 which comprises fractionally liberating the enantiomers from the diastereomer salts.

4. A process as claimed in claim 1 which further comprises liberating the enantiomers from the filtrates of the salt formation steps.

5. A process as claimed in claim 1 which further comprises purifying the enantiomers prepared by resolvation or their salts formed with the achiral reagent by recrystallization.

6. The process defined in claim 1 wherein in the compound of the Formula (I) R is hydrogen, formyl or acetyl.

7. The process as defined in claim 1 wherein the enantiomers are liberated from the diastereomer salts by treating the diastereomer salts with aqueous hydrochloric acid to precipitate from the diastereomer salts the resolving agents of the Formula (II) and which further comprises filtering off and drying the precipitated resolving agent to recover same for further use.

8. A compound selected from the group which consists of:
L-phenylalanine-D-N-benzoyl-phenylalanine salt, D-phenylalanine-L-N-benzoyl-phenylalanine salt, D-phenylalanine-O,O-dibenzoyl-L-tartaric acid salt, D-phenylalanine-O,O-di-p-toluoyl-L-tartaric acid salt, L-N-formyl-phenylalanine-D-2-benzylamino butanol salt, and L-N-acetyl-phenylalanyl-D-phenylglycine amide salt.

* * * * *